US008729278B2

(12) United States Patent
de Munck et al.

(10) Patent No.: US 8,729,278 B2
(45) Date of Patent: May 20, 2014

(54) PHTHALIC ANHYDRIDE PROCESS

(75) Inventors: Nicolaas A. de Munck, Barendrecht (NL); Raul Zweevel, Capelle aan den Ijssel (NL); Annemieke de Winter, Bergen op Zoom (NL); Liza De Geeter, Kontich (BE); Theo Wandel, Hellevoetsluis (NL)

(73) Assignee: ExxonMobil Chemical Patents Inc., Houston, TX (US)

( * ) Notice: Subject to any disclaimer, the term of this patent is extended or adjusted under 35 U.S.C. 154(b) by 107 days.

(21) Appl. No.: 13/378,925

(22) PCT Filed: Oct. 13, 2010

(86) PCT No.: PCT/EP2010/065310
§ 371 (c)(1),
(2), (4) Date: Jun. 26, 2012

(87) PCT Pub. No.: WO2011/051102
PCT Pub. Date: May 5, 2011

(65) Prior Publication Data
US 2012/0259131 A1 Oct. 11, 2012

(30) Foreign Application Priority Data
Oct. 26, 2009 (EP) .................................... 09013464

(51) Int. Cl.
*C07D 307/89* (2006.01)
*C07C 69/74* (2006.01)

(52) U.S. Cl.
USPC .......................................... 549/248; 560/127

(58) Field of Classification Search
USPC ........................................... 549/248; 560/127
See application file for complete search history.

(56) References Cited

U.S. PATENT DOCUMENTS

| 4,411,705 A | 10/1983 | Easley, Jr. et al. |
| 4,568,029 A | 2/1986 | Newton et al. |
| 4,994,241 A | 2/1991 | Sapoff |
| 2002/0139396 A1* | 10/2002 | Yunoki .......................... 134/10 |
| 2005/0109377 A1 | 5/2005 | Schliephake et al. |

FOREIGN PATENT DOCUMENTS

| EP | 1 226 865 | 7/2002 |
| WO | 93/00159 | 1/1993 |
| WO | 98/00239 | 1/1998 |
| WO | 2004/058572 | 7/2004 |
| WO | 2006/131556 | 12/2006 |
| WO | 2006/131557 | 12/2006 |
| WO | 2009/040245 | 4/2009 |
| WO | 2009/040246 | 4/2009 |
| WO | 2011/051102 | 5/2011 |

* cited by examiner

Primary Examiner — T. Victor Oh
(74) Attorney, Agent, or Firm — Andrew B. Griffis

(57) ABSTRACT

Disclosed is an improved process for the production of phthalic anhydride wherein the spent catalyst is removed from the oxidation reactor tubes more effectively by vacuuming from the top and using a vacuum hose having a tip with an increased impact strength and with a maximum hardness. As a result, the new catalyst loading can be made more uniform and the process may be operated with improved stability at higher organics loadings in the reactor feed. Process stability may be further improved by varying the outlet temperature of the phthalic anhydride precondenser over time.

14 Claims, No Drawings

US 8,729,278 B2

PHTHALIC ANHYDRIDE PROCESS

CROSS-REFERENCE TO RELATED APPLICATIONS

This application is a 371 National Stage Application of International Application No. PCT/EP2010/065310, filed Oct. 13, 2010, which claims the benefit of EP 09013464.4, filed Oct. 26, 2009, the disclosures of which are herein incorporated by reference in their entireties.

FIELD OF THE INVENTION

The present invention relates to improvements in or relating to the process for the production of phthalic anhydride, more particularly in improving the safety and the reliability of the process by an improved method for the removal and replacement of used heterogeneous oxidation catalyst from a tubular reactor that was operated as part of such process, and by an improved method of operating the liquid condenser that may be located downstream of the oxidation reactor.

BACKGROUND OF THE INVENTION

Phthalic anhydride (PAN) is an important intermediate chemical in the chemical industry. One important use is in the production of alkyl phthalates such as di-isononyl or di-isodecyl phthalates which are used as plasticisers typically for polyvinyl chloride. These phthalates may be further hydrogenated to the corresponding di-cyclohexanoates. Phthalic anhydride has been produced on an industrial scale for many years. Phthalic anhydride is typically produced on a commercial scale by the vapour phase oxidation of primarily ortho-xylene (o-xylene), or less frequently of naphthalene, over a heterogeneous metal oxide catalyst. Typically air is used as the oxidant and the process generally uses a vanadium oxide catalyst, more specifically vanadium pentoxide on a support.

After the reaction, the reaction product vapour mixture containing the crude phthalic anhydride that has been produced passes to a cooling stage where it is cooled, generally by a gas cooler, and is subsequently passed to optionally a liquid condenser and finally to a switch condenser for condensing the PAN. Finally the condensed phthalic anhydride is subjected to a purification or finishing step. Phthalic anhydride processes are disclosed in more detail in WO 2009/040245 and WO 2009/040246.

The efficiency of a phthalic anhydride plant is measured in terms of the number of grams of ortho-xylene that can be processed for each normal cubic meter of oxygen-containing gas or air that is fed to the raw material section (known as the loading). The greater the amount of ortho-xylene per unit of gas flow, the greater is the efficiency of the facility. Considerable attempts have been made over the years to increase the loading, and loadings above 80 gram/Nm$^3$ of ortho-xylene in air have been reported.

The oxidation reaction is highly exothermic. The process typically operates with reaction mixtures of the vaporised organic material in air, at temperatures higher than 300° C., and the mixtures have compositions that are typically inside the explosive range, and this generally all through from reactor feed to effluent. The reaction conditions need to be controlled very tightly in order to minimize the occurrence of local excessive exotherms, which can cause the reaction mixture to detonate. The reaction is most commonly performed in a tubular reactor, i.e. a reactor designed as a tube-and-shell heat exchanger, with the catalyst located as a fixed bed of particles inside the tubes, and a molten salt bath circulating on the shell side for removal of the reaction heat. The reactor tubes typically have a length of at least 3 meters, and a typical internal diameter of about 25.4 mm (1 inch). The reactor feed typically enters the reactor tube at the top and flows down towards the bottom.

In order to further improve process stability, and save energy in compressing the air for the reaction, the reaction pressure is preferably kept low, which means that a low pressure drop is desired over the catalyst bed itself and over the equipment downstream thereof, such as over the phthalic anhydride condensers. In order to provide a low pressure drop over the catalyst bed, commercial catalysts have since decades adopted a ring-type or hollow cylinder design, whereby the active catalyst is coated as a thin active layer onto the (inner and) outer surface of a ring-type inert support, usually of ceramic material. The preferred catalyst is composed of a mixture of vanadium pentoxide, titanium dioxide, and several other metal, alkali and earth-alkali components in varying concentrations, typically coated on a ceramic ring or hollow cylinder material. Such a hollow cylinder may e.g. have 7 mm as the outer diameter (OD) and 4 mm as the inner diameter (ID), and have a height (H) of 7 mm. Alternatively, the cylinder may have 8×6×5 mm as (OD×H×ID) dimensions.

The active layer coating typically contains an organic binder and/or adhesive to help in keeping the layer in place on the surface of the inert support. During the initial startup and the subsequent operation of the catalyst at the typical operating conditions, the organic binder and/or adhesive typically disintegrate and disappear. The catalytically active material remains in place as a thin and fragile layer, which may rapidly fall apart into a powder form upon exposure to mechanical action and/or upon exposure to a liquid when it may readily form a slurry.

A commercial phthalic anhydride process may typically employ more than 10,000 vertically mounted tubes per reactor, and the flow of the reaction mixture needs to be well distributed over the many reactor tubes. This reduces the risk for local temperature excursions, and by which process stability improves. It also reduces differences in the conversion levels reached over the individual tubes, such that the reactor may be operated closer to the desired conversion level and product quality problems, because of byproduct formation, are reduced. Because of the low pressure drop available during operation over the oxidation reactor, this requires a close similarity in the composition and structure of the catalyst bed in each of the reactor tubes.

The catalyst slowly looses activity through its use, and typically the salt bath temperature, and thereby the reaction temperature, is then carefully adjusted upwards to compensate for the activity loss. This may be done up to a level where side reactions and byproduct formation have become excessive, at which point the catalyst is considered at the end of its life. Usually after several years in operation, such as after 3 or 4 years, the now spent catalyst needs to be removed and replaced by catalyst having a higher activity and/or selectivity, typically with fresh catalyst.

The vanadium in the spent catalyst is highly valuable, and is typically recovered and reused. Also the inert support represents sufficient value, such that its recovery and reuse is of high interest. A good separation is therefore important of the active material containing the vanadium from the inert support. The active material is typically recovered as a slurry of active material powder in a liquid phase, usually by washing the spent catalyst with water, and it is important for an efficient recovery and recycling of the vanadium metal that contamination of the slurry with inert powder, such as with dust originating from the inert support, is minimised. The reuse of the inert support is also improved if physical damage to the support particles, in particular during the removal of the spent catalyst from the reactor, is minimised.

In order for the new catalyst bed to be loaded correctly and similar to the other reactor tubes, it is important that the tubes of the reactor are empty and clean prior to the loading. WO 2006/131557 discloses a method for controlling the unloading of the catalyst from a tubular reactor by using one or more light sources.

Unloading the catalyst from the bottom of a tubular reactor has several problems, in particular when the catalyst is not free-flowing and needs to be dislodged in order to release from bridging between particles or from the tube wall, such as described in U.S. Pat. No. 4,411,705. An alternative is to have personnel enter the bottom section of the reactor, below the bottom tubesheet, and after having removed the support for the catalyst bed, poke the underside of the catalyst bed with a metal wire to dislodge the catalyst particles and have them fall from the bottom of the tube.

WO 2006/131556 discloses that an incorrectly filled tube, in a tubular reactor such as in a phthalic anhydride process, must be identified from the bottom tubesheet in order to allow emptying the tube from the bottom.

It is typically impractical or impossible to remove the bottom head of the reactor, so the space below the bottom tubesheet of the tubular reactor is typically a confined space and only accessible through a manhole. During catalyst unloading from the bottom, any personnel accessing the bottom tubesheet, to for instance remove the bed support, may come in contact with a stream of falling catalyst particles. In addition, the particles may be accompanied by dust, and more dust may be formed when the catalyst pellets fall onto a solid surface. Dust is a problem of industrial hygiene, and the catalyst dust may be particularly problematic because of its possible toxicity, a.o. because of the vanadium content. The bottom space of the reactor during unloading of the catalyst from the bottom therefore becomes an inhospitable confined space of limited dimensions, wherein personnel typically needs to wear personnel protection equipment such as a breathing apparatus.

In order to overcome the need for personnel to enter the inhospitable space inside a reactor, U.S. Pat. No. 4,411,705 discloses the dislodging of used catalyst inside the tubes of a tubular reactor in the petrochemical industry by means of a string or burst of missiles, from the bottom of the reactor until all of the catalyst has fallen from a tube. At the same time a gas may be caused to flow down the tube to induce the particles to flow down the tube. The falling used catalyst particles are preferably collected in a particle collector under the tube, from which they may be removed by attaching a vacuum tube.

This use of missiles from the bottom to dislodge the catalyst particles and have them fall out the bottom of the tube is a complex operation, for instance because it needs to be assured that all tubes have been treated by the missile gun and have successfully been emptied. When launching the missiles from the bottom of the tube, it is difficult to at the same time also collect the fallen particles and the dust from underneath the bottom tubesheet.

Because of the complexity of the method of unloading the catalyst from the bottom, it is preferred to unload the catalyst from the top. The catalyst particles may be vacuumed out from each of the tubes by entering the reactor tube with a smaller vacuum tube, through which the catalyst particles are then vacuumed up.

The particles of the catalyst often become bridged through their use in service. They typically need to be dislodged before they may be vacuumed out. Dislodging the particles during the vacuuming is conveniently done by mechanical action with the vacuum tube, provided the vacuum tube is made from a rigid construction material.

The vacuum tube is usually made longer than the reactor tube, such that it is able to reach all the way from above the top of the reactor tube down to the bottom of the tube. Because of weight and ease of handling, the vacuum tube is therefore conveniently made from a light weight material, typically from rigid PVC.

We have now found that the vacuuming out of catalyst from the tubes of a phthalic anhydride reactor using a rigid PVC vacuum tube still poses problems. For exchanging the catalyst, the reactor top head is usually removed and a tent or cabin is mounted covering the top tubesheet of the reactor, in order to protect the personnel performing the catalyst exchange, and the material and equipment they are handling, from adverse weather conditions. With the rigid PVC vacuum tube, the inner height of the tent or cabin above the top reactor tubesheet needs to be longer than the length of the vacuum tube, allowing sufficient manoeuvring with the vacuum tube. The total height of the tent or cabin becomes large, which puts extra requirements on its construction, for instance because of wind exposure.

Also, by the mechanical action with the vacuum tube to dislodge the catalyst particles, pieces are chipped off from the tip of the vacuum tube, and the vacuum tube mouth looses its integrity. This makes the vacuuming less effective and increases the time required for emptying the reactor, and thus for the catalyst change out. A longer catalyst change out is at the expense of time on stream for the reactor, and thus of plant capacity. The reduced efficiency of the vacuuming reduces the effectiveness of the dust removal during the vacuuming and increases the time during which personnel may become exposed to catalyst dust.

A deformed vacuum tube mount also increases the risk to leave catalyst particles and/or scale sticking to the reactor tube wall, which if not removed before loading the new catalyst, may cause higher pressure drop over some of the tubes and/or local channelling of the flow of the reaction mixture, which creates an inherent risk for process instabilities.

The vacuum tube also becomes shorter and needs to be replaced when it has become too short to reach the bottom of the reactor tube. This is usually noticed when the reactor tube still contains catalyst and catalyst dust, and such replacement of a vacuum tube further increases the risk for undesired exposure of the personnel to catalyst dust. In addition, the pieces of rigid PVC breaking from the vacuum tube are vacuumed up with the catalyst particles. The collected used catalyst becomes contaminated and this makes the recovery of the metals from the used catalyst, and of the inert catalyst support, more difficult.

WO 93/00158 discloses a method for catalyst unloading of tubular reactors, whereby an flexible air lance is introduced into the reactor tube and high pressure gas is injected through a jet to dislodge the catalyst and to blow the fluidized catalyst out of the top of the tube, where a high volume vacuum source creates a negative pressure in a plenum chamber located on top of the tube, through which the catalyst is removed. WO 93/00158 describes this method to be applicable to reactors used in a variety of processes, including in the production of phthalic anhydride.

WO 98/02239 describes a similar method for emptying a tube reactor, such as ethylene oxide, acrylic acid or terephthalic acid reactors. In this method, the bottom end of the reactor tube to be emptied is first temporarily sealed, after which from the other end a flexible pressure pipe is introduced into the reactor tube and gas under pressure is injected through a nozzle in order to detach the catalyst particles, which are then sucked up by a suction pipe which is connected to the top of the reactor tube to be emptied.

In these methods, the use of high pressure gas injection and of seals at the connections of the vacuum pipe to the reactor tube and around the pressure pipe or lance cause significant risks for catalyst dust to escape, which is a safety and industrial hygiene problem for the workers involved in the catalyst removal.

U.S. Pat. No. 4,568,029 discloses a process for unloading catalysts from multi-tube reactors. The process can employ steel rods, gravity and air jets. No hose together with a vacuum is applied.

US 2005/0109377 discloses the removal of catalyst from the tubes of a tube bundle heat exchanger by inserting a rotating drill driven by a drilling machine into the tube, the drill having a steel shaft and a drill tip provided with teeth made of stellite, and using a rotation rate of 220 to 280 rpm. This method is proposed for the cleaning of tubes in which the catalyst solids are no longer present in loose particulate form, but rather at solid blocks, and/or are adhering particularly firmly to the inner walls of the tubes. US 2005/0109377 proposes this method for a variety of heterogeneously catalyzed partial oxidation processes, such as the conversion of o-xylene or naphthalene to phthalic anhydride. This method however causes excessive physical damage to the catalyst particles used in the production of PAN, such that the inert support recovered from the spent catalyst cannot be recycled. In the comparative example of US 2005/0109377, an attempt to suck out the tubes of a reactor by means of a suction tube which consisted of a plastics hose having, mounted at the tip, an 80 cm-long metal tube cut obliquely and having 85% of the reaction tube diameter, was unsuccessful.

There therefore remains a need for a method to remove the spent catalyst from a phthalic anhydride process that allows recovery and reuse of the vanadium and of the inert support particles.

EP 1226865 A2 discloses the removal of catalyst from a shell-and-tube reactor used in a many catalytic reactions. In this method, an aspirating tube, connected to an exhaust gas aspirator, is inserted from the top into a reaction tube in order to remove the catalyst together with a stream of air. The aspirating tube may have high rigidity and may be difficult to deform, or it may have flexibility and can be bent. EP 1226865 discloses that an aspirating tube made of polyethylene has good workability and can easily be used because of properly bending. In a variant of the method, the kind of material or shaped structure at the tip portion of the aspirating tube can be different from that of the rear portion. The use of an aspirating tube consisting of a polyethylene tube is exemplified in EP 1226865 for extracting catalyst from a process for producing methacrylic acid from methacrolein, and from a process for producing acrylic acid from propylene. In one example the aspirating tube was provided, to the side where the aspirating tube for extraction was inserted to the reaction tube, with a stainless steel adaptor which was cut to form an end surface having a hollow portion.

We have also found that when using a vacuum hose made of rigid PVC, a static electricity charge tends to build up on the vacuum hose, which may transfer to the personnel handling the vacuum hose. The static electricity charge accumulated in the person may then discharge, and reduce the working comfort of the personnel performing the vacuuming operation.

There therefore remains a need for further improving the phthalic anhydride process to improve its operating stability and to increase its capacity. The present invention is concerned with this problem. The invention is further concerned with improving the industrial hygiene conditions and the working comfort of the personnel involved in the catalyst change out from the reactor. The invention is further concerned with improving the recovery and the reuse of the vanadium metal and of the inert support particles from the spent catalyst of the PAN process.

The present invention aims to obviate or at least mitigate the above described problem and/or to provide improvements generally.

SUMMARY OF THE INVENTION

According to the invention, there is provided a process as defined in any of the accompanying claims.

The current invention improves the operating stability and capacity of the phthalic anhydride process primarily by improving the method for catalyst removal after it has reached the end of its commercial life.

The invention provides for a process for the production of phthalic anhydride comprising contacting a gaseous mixture of ortho-xylene or naphthalene and an oxygen-containing gas with an oxidation catalyst comprised in vertical tubes of a tubular reactor, the process comprising after using the catalyst taking the tubular reactor out of production service, removing the used catalyst and loading more active catalyst into the reactor tubes, whereby used catalyst is removed from the reactor tubes by vacuum hosing through a vacuum hose or tube that is introduced into the reactor tube from the top and characterised in that the tip of the vacuum hose or tube comprises a material that has (i) a notched Izod impact strength, according to ASTM D256, of at least 55 J/m, preferably at least 60 J/m, more preferably at least 90 J/m, even more preferably at least 190 J/m and optionally at most 1500 J/m, preferably at most 1400 J/m, more preferably at most 1000 J/m and even more preferably at most 500 J/m, or a U-notched Charpy impact strength at 23° C., according to ISO 179, of more than 5 kJ/m², preferably at least 5.5 kJ/m², more preferably at least 6 kJ/m², most preferably at least 7 kJ/m², and optionally at most 49 kJ/m², preferably at most 45 kJ/m², more preferably at most 30 kJ/m², even more preferably at most 23 kJ/m² and most preferably at most 15 kJ/m², and (ii) a Shore D hardness, according to ISO 868 or ASTM 2240, of at most 90, preferably at most 83 and more preferably at most 80.

According to the invention, the material for the tip of the vacuum hose or tube has an impact strength or resistance that is higher than this of unmodified rigid PVC, and has a hardness, here expressed as Shore D hardness, that is lower than this of stainless steel.

The advantage of the present invention, in particular of the balance of material properties used for the vacuum tube or hose, is that the vacuum tube or hose used for removing the catalyst from the reactor does not loose its integrity at the tip, as compared to unmodified rigid PVC. The vacuuming of catalyst particles may then maintain its full effectiveness and the catalyst may be removed from the reactor in a shorter time period, which shortens the total catalyst change out time, the time the reactor needs to be decommissioned for the change out, and therefore increases the time the reactor may be on stream for phthalic anhydride production, and thus plant capacity. The better maintained integrity of the tip of the vacuum hose also results in less catalyst particles and dust remaining stuck to the wall of the reactor tube after the vacuuming operation. With the spent catalyst more effective removed, the new catalyst loading may be made more uniform, and the flow distribution over the many reactor tubes, and hence the stability of the phthalic anhydride process may be further improved. Further, contamination of the used spent catalyst collected from the catalyst change out by chips of rigid PVC is eliminated.

At the same time, the hardness of the material for the tip of the vacuum hose or tube is lower than this of stainless steel. This brings the advantage that the catalyst particles undergo less physical damage during their removal from the reactor tube and as a result of the mechanical action by the operator to dislodge the catalyst particles. This improves the recovery and recycling of both the active material and of the inert support particles of the oxidation catalyst. Less dust formed from damaging the inert support particles increases the quality of the powder containing the vanadium metal of the spent catalyst, and less damage to the inert support particles increases their suitability for reuse.

The product mixture obtained from operating the oxidation reactor is typically routed first to gas coolers and then to condensers that remove the phthalic anhydride product from the rest of the mixture. Usually parallel switch condensers are used for that purpose, which obtain the phthalic anhydride as a solid by (de)sublimation from the reaction product vapour in a heat exchanger using a cooling fluid, such as a heat resistant oil, to remove the sublimation heat. After collecting an amount of solid in the switch condenser, the heat exchanger is usually taken out of service, and the cooling service is switched to heating service, typically using the same fluid but which now is heated by an external source to provide sufficient heat to melt the solid phthalic anhydride, which may then be drained from the switch condenser, collected and taken for further processing and/or storage. After draining the switch condenser, its duty may be returned to cooling and it may be reintroduced into the process mainstream for removing phthalic anhydride from the reaction product.

The phthalic anhydride process may also comprise one or more liquid condensers, usually located upstream of the switch condensers, in which a first part of the phthalic anhydride in the reactor product may be condensed as a liquid, and this liquid may then be drained from the liquid condenser, also known as the precondenser. These liquid condensers are typically operated in continuous mode, and are usually not removed from service unless the oxidation reactor is also decommissioned.

We have now found that a further process stability improvement may be achieved by an improved operation of the liquid (pre-)condensers, whereby its outlet temperature is first raised and subsequently returned to its original level. This allows stabilising the pressure drop over the liquid precondenser at a low and acceptable level such that a lower reactor pressure may be maintained and more stable operation is achieved at a higher organics loading in the process.

DETAILED DESCRIPTION

The o-xylene or naphthalene in a phthalic anhydride production process is typically preheated and sprayed as a hot liquid into preheated air, in order to form a mixture of vaporised o-xylene in air that is then fed to the oxidation reactor. In modern plants, the mixture composition is typically significantly inside the flammability range. The lower flammability limit of an o-xylene mixture in air is reached with a loading of 42 grams per $Nm^3$ of air, and the modern commercial plants operate at loadings of at least 80, preferably 90 and sometimes even 100 grams per $Nm^3$. Any ignition source in contact with the vapour mixture may thus cause a deflagration which, if not properly handled, may lead to a detonation.

Excessive temperature excursions may be sufficient to act as ignition sources for such deflagrations. Tight control of the reaction temperature is therefore imperative for operating the process safely. Therefore a tubular reactor is typically employed, with the catalyst stacked as a fixed bed of particles in reactor tubes around which circulates a heat transfer fluid, typically a molten salt bath, transferring the heat of the reaction to typically a heat exchanger where it is used to generate steam. The temperature of the salt bath is then controlled very closely.

An improved phthalic anhydride process is disclosed in WO 2009/040245, wherein process stability is improved by employing spray nozzles with a surface of higher hardness, such that erosion is minimised and the resulting vapour/gas mixture is more homogeneous. Another improvement of the process stability may be obtained, as disclosed in WO 2009/040246, by avoiding condensation of vaporised ortho-xylene from the vapour/gas mixture on its path to the oxidation reactor.

The present invention is concerned with further improving the stability of the phthalic anhydride process, on one hand by improving the removal of spent catalyst from an oxidation reactor after service, such that the new catalyst may be loaded more uniformly and the reactor feed during operation is more evenly distributed over the many reactor tubes, and on the other hand by improving the operation of the precondenser, if present downstream of the oxidation reactor, such that its pressure drop is stabilised at a low and acceptable level to continue operating the process at higher organics loading.

Turning to the catalyst unloading, we prefer to unload the spent catalyst from a phthalic anhydride reactor from the top. The top head from a tubular phthalic anhydride reactor typically needs to be removed anyway to allow good access to the top tubesheet for a proper loading of new catalyst into the tubes. The top head is therefore usually designed for removal and easier to remove than the bottom head. With the reactor top head removed, access to the top tubesheet with a vacuum hose or tube becomes simple.

Mechanical action of the vacuum hose or tube, inserted into the reactor tube from the top for removing the catalyst particles, is able to dislodge the top layer of catalyst particles in the catalyst bed, so that the particles come loose from any bridging between particles or with the tube wall, and the particles may be sucked up by the vacuum hose or tube. The mechanical action should not cause damage to the catalyst support material as it otherwise becomes unsuitable to be recycled for future use as support for a new catalyst. Any catalyst dust present in the catalyst bed is sucked up at the same time. Any catalyst dust formed during transport of the particles through the vacuum hose or tube is also transported by the air flow in the same direction as the catalyst particles. The operation therefore minimises exposure of operating personnel to catalyst dust. This advantage is better maintained with the process of the present invention because the integrity of the tip of the vacuum hose or tube is maintained better and longer than with conventional and more brittle materials.

Impact strength and impact resistance are used interchangeably throughout this document. The notched Izod impact strength or the U-notched Charpy impact strength are typically measured according to the standards given, and at room temperature, which is typically set at a standard of 23° C.

The impact strength preferably is below at least one of the specified maxima, because that improves the effectiveness of the mechanical action with the vacuum tube or hose in dislodging the catalyst particles as compared with tip materials having lower impact strength, because a gain in impact strength of e.g. a plastic material may also increase the elastic modulus and lead to materials which become too flexible and thus less effective in transferring the mechanical action from the vacuum tube to the catalyst particles.

In an embodiment of the present invention, the body of the vacuum hose or tube comprises a material having an elastic or flexural or Young modulus, according to DIN EN ISO 527, of less than 2.7 GPa, preferably at most 2.6 GPa, more preferably at most 2.5 GPa, even more preferably at most 2.4 GPa and optionally at least 200 MPa, preferably at least 390 MPa, more preferably at least 1 GPa. For many materials, it is the tangent tensile modulus value that is typically reported as the Young modulus or modulus of elasticity.

The advantage of a vacuum hose with a flexural modulus as specified is that the vacuum tube is more flexible than rigid PVC, such that it may readily be curved and the piece of the vacuum tube sticking out above the reactor tubesheet does not need to be kept straight and almost vertically up. When the vacuum tube or hose above the reactor tubesheet may be curved sideways, the inner height of the tent or cabin mounted above the top reactor tubesheet may be reduced to below the length of the vacuum tube, and still allow sufficient manoeuvring with the vacuum tube. The total height of the tent or cabin may become smaller, reducing the construction requirement due to wind exposure. It may even allow for performing the catalyst removal without having the need to remove the reactor top head. The flexural modulus preferably is above the specified minimum because this improves the effectiveness in transferring the mechanical action exerted by the operator to the vacuum tube down the reactor tube and from the vacuum tube to the catalyst particles.

In another embodiment, the body of the vacuum hose or tube comprises a material having an electrical resistivity at room temperature of at most $10^{15}$ Ohm.cm, preferably at most $10^{14}$ Ohm.cm, more preferably at most $10^{13}$ Ohm.cm, even more preferably at most $10^{12}$ Ohm.cm, yet more preferably at most $10^{11}$ Ohm.cm and even more preferably at most $10^{10}$ Ohm.cm. Most preferred is a material with even lower electrical resistivity, such as at most $10^{9}$ Ohm.cm.

We have found that this reduces the buildup of electrostatic charges on the vacuum tube, which may transfer on to the personnel handling the vacuum tube, and improves the comfort of the personnel performing the vacuum operation.

In yet another embodiment of the present invention, the Shore D hardness of the material comprised in the tip of the vacuum hose or tube, according to ISO 868 or ASTM 2240, is at least 40, preferably at least 50, more preferably at least 60, even more preferably at least 70.

This brings the advantage that the mechanical action with the vacuum tube is more effectively transferred to the catalyst particles, such that the particles are more readily dislodged and may be vacuumed out at a faster rate. An additional advantage is that the vacuum tube has sufficient rigidity such that, at the end of vacuuming out a reactor tube, the operator may use the vacuum tube to also push out the catalyst support from the bottom of the tube. The pushed out supports may collect and later readily be recovered from inside the reactor bottom head with minimal need for personnel to enter into the reactor bottom compartment. The catalyst support is porous to let the process stream pass, and we conveniently use as catalyst support a conical helicoidal metal spring, such as produced by Augsburger Federnfabrik GmbH, Boschstrasse 1, D-86343 Koenigsbrunn Germany, because these are easy to insert into the bottom of the tube in a minimum of time, provide sufficient support for the catalyst bed, and may be pushed out from above by mechanical action with the vacuum tube according to the present invention.

The rest of the tube cleaning, inspection and loading procedure for more active catalyst is fully targeted towards ending up with catalyst beds in each of the many reactor tubes that are all loaded as correctly as possible and in a similar fashion in all the tubes, i.e. with minimal deviations from each other. This target is to assure that, during subsequent operation of the process, the flow of the reaction mixture is about the same through each of the reactor tubes, such that the process remains stable at higher loadings of organics in the mixture being fed to the oxidation reactor, and thus at higher throughput or capacity. In addition, thanks to the good flow distribution, the overall pressure drop over the reactor may be kept low, which further improves the stability of the process.

The vacuum hose or tube typically connects at the output end into a wider collection compartment, where, because of the air velocity being reduced, most of the particles and a part of the dust are allowed to collect in the bottom of the compartment. The air is then usually filtered before returning it to the atmosphere at a safe location.

When the catalyst particles are removed from the reactor tubes by vacuum hosing from the top of the reactor tube, any dust formed during the unloading operation is typically also removed by the vacuuming system, and the risk of dust exiting the reactor tube, especially from the top of the tube where the personnel is located, is minimised. The possible exposure of personnel performing the unloading to catalyst dust is therefore reduced. For this purpose, we conveniently use a vacuum hose or tube having an outer diameter that is relatively large, such that it leaves only a relatively small cross-sectional area between the vacuum hose and the inner wall of the reactor tube. The air being sucked into the top of the reactor tube around the vacuum tube or hose then moves faster, giving less chance for catalyst dust to escape. On the other hand, a too large diameter of the vacuum tube increases the pressure drop taken by the air on its way down the reactor tube around the vacuum hose, and reduces the air flow up inside the vacuum hose, which impairs the effectiveness of the vacuuming operation. We therefore conveniently use a vacuum hose or tube of which the outer diameter is at most 88% of the inner diameter of the reactor tube, preferably at most 85%, even more preferably at most 83% and most preferably at most 80% of the inner diameter of the reactor tube. For reactor tubes having an internal diameter of 25.4 mm, we therefore conveniently use a vacuum hose or tube having an outer diameter of at least 15 mm, preferably at least 18 mm, more preferably at least 19 mm, even more preferably at least 20 mm, yet more preferably at least 21 mm and optionally 22 mm.

It is also important that particles or small agglomerates of particles flowing up inside the vacuum tube or hose keep moving and do not become stuck. We therefore conveniently use a vacuum hose or tube that has an inner diameter that is at least 2 times the catalyst particle diameter, preferably at least 2.5 times and more preferably at least 3 times the catalyst particle diameter. Our preferred vacuum tube for the reactor tube having an internal diameter of 25.4 mm has an internal diameter of at least 14 mm, more preferably at least 15 mm, even more preferably at least 16 mm, yet more preferably at least 17 mm, and most preferably at least 18 mm, for a catalyst having the shape of a hollow cylinder and an outer diameter of 7 mm.

In an embodiment, the vacuum hose or tube and/or the tip of the vacuum hose or tube comprises a material selected from the family of plastics or of polymers, because of the balance of properties these may provide, such as from the group consisting of polyamide, impact modified unplasticised PVC, flexible PVC, ABS, epoxy, fluoropolymer, polycarbonate, polyester, polyether imide, polyethylene, polypropylene, polystyrene, polysulfone, polyurethane, thermoplastic polyurethane, polyacetal, and mixtures thereof, preferably comprises polyamide. We conveniently use polyamide DIN 11/12 according to DIN 73378 as the material for the tip, such as provided by Hansa-Flex AG, Zum Panrepel 44, 28307 Bremen, Germany.

In an embodiment of the present invention, the materials comprised in the body and in the tip of the vacuum hose or tube are the same; preferably the vacuum hose or tube is made entirely, meaning body and tip, of the same material. This brings the advantage of easier construction and avoids the need for a connection between the tip and the body of the vacuum hose or tube, which may unintentionally disconnect during vacuuming upon which the tip may have to be recovered before the removal of the catalyst from the reactor tube can be continued further. We have found that several of the named materials are suitable for the tip as well as for the body of the vacuum tube or hose according to the present invention. We prefer to use a vacuum tube of which the body and the tip are made in one piece and with the tip inseparable from the body of the tube, and more preferably made from polyamide DIN 11/12 according to DIN 73378.

The tip of the vacuum hose or tube of the present invention may have many different shapes, such as for instance those proposed in EP 1226865 A2. We have found that it is very convenient, especially when the vacuum tube is made in one piece from the same material, to have the tip of the vacuum hose or tube form a plane that is not perpendicular to the longitudinal axis of the hose or tube itself. We conveniently have the tip of the vacuum hose or tube forming a plane that is slanted in an angle with the longitudinal axis of the hose or tube, and in which the angle is in the range of 20-70°, more preferably in the range of 30-60°, even more preferably in the range of 40-50° with the longitudinal axis of the hose or tube.

Most preferred is an angle of about 45°. This tip shape may be readily obtainable by cutting the end of the vacuum hose appropriately. We have found that this tip shape allows concentrating the mechanical action of the vacuum hose at the longer end of the hose, it allows to move the longer end of the vacuum hose around the perimeter of the reactor tube by turning the vacuum hose around its longitudinal axis, and it reduces the risk that particle agglomerates become stuck in the mouth of the vacuum tube or hose. We have also found that this tip shape is very effective in pushing out the conical spring that is typically used as support for the fixed bed inside the reactor tube.

After the used catalyst has been vacuumed from the reactor tube according to the present invention, we usually further clean the inside of the reactor tube to remove any remaining catalyst particles and dust, and/or scale built up during the operation of the reactor. This is to further assure that the reactor tubes are empty and clean prior to the loading of the new catalyst. We conveniently perform this cleaning by mechanical action from one end of the reactor tube, preferably from the top of the reactor tube, and by that mechanical action remove any remaining catalyst or other solid material from the inside of the reactor tube.

An alternative method for cleaning the reactor tubes further, after removal of the catalyst particles, is by a wet method, whereby the tubes are washed with water, demin water or condensate followed by drying with air, hot air or nitrogen. Another alternative method is to apply sand or grit blasting, whereby particularly hard scale can be removed from the tube-wall. We prefer to use the dry method because it brings several advantages. We have found that the dry method is more effective in cleaning the tube, as it also removes scale from the reaction which may not be water soluble. Mainly because also water insoluble matter is removed, the dry method also achieves a smoother inner surface of the reaction tubes, such that a better packing can be achieved of the new catalyst loading. The dry method also avoids any corrosion risk, and avoids the need to dry the reactor tubes after the cleaning.

We conveniently use brushing as the mechanical action for cleaning, and we prefer to use a steel brush for that purpose, more preferably a stainless steel brush. Steel brushes provide the mechanical properties and strength to withstand the forces applied on the brush and encountered when in contact with the reactor tube, the catalyst particles and/or the scale or other solid material inside the tube. Steel brushes also better withstand against mechanical wear. Stainless steel brushes are sufficiently soft and ductile, and provide a lower risk for spark generation during their use. The brush conveniently is a rotating brush, and we prefer to drive the rotating brush by an air motor, such that the risk for ignition of any hydrocarbons that may have been entrapped in the catalyst bed and may release during the cleaning operation is minimised. We prefer to use single knitting stainless steel brushes.

During the cleaning of the reactor tubes, we prefer to apply a vacuum on the reactor tube that is being cleaned, so that particles and dust being formed or loosened from the wall are being removed immediately. We usually apply this vacuum from the other end from which the mechanical action for the cleaning is performed. Typically the mechanical cleaning action is performed from the top of the tube, and the vacuum is then applied from the bottom of the tube. This again minimises the risk of exposure of personnel performing the cleaning action with catalyst particles and/or dust, or with hydrocarbons.

When the reactor tubes are supposed to be empty and clean, we conveniently push through each of the reactor tubes a flexible or compressible plug having a diameter slightly higher than the tube internal diameter. This adds an extra cleaning step when the plug passes through the tube. The plugs preferably have mechanical properties and dimensions such that they get stuck at a location where the vacuuming and/or cleaning has been incomplete and solid material has remained stuck to the tube wall. We usually push the plug through the tube starting from the end of the reactor tube from which the mechanical action is performed. We typically use a foam or a felt plug. We conveniently assist the pushing of the plug by applying air pressure at the starting end, and/or by applying vacuum at the receiving end of the reactor tube. Applying the vacuum further reduces the risk of exposure of personnel to catalyst particles or dust, or hydrocarbons. We prefer the plug to have in its unstrained form at least one circular cross section, more preferably being cylindrical in shape, and preferably the circular cross section having a diameter of at least the internal diameter of the reactor tube, more preferably at least 105% of the reactor tube internal diameter. This improves the contact between the tube wall and the plug, such that the cleaning action is optimised and the chance of being stuck at an unclean spot in the tube is increased. We prefer that the diameter of the circular cross section of the plug in unstrained form is at most 200% of the internal diameter of the reactor tube, preferably at most 150%, even more preferably at most 125% and most preferably at most 115% of the internal diameter of the reactor tube. This depends upon the material, the compressibility and the physical shape of the plug. We prefer that the diameter of the circular cross section of a felt plug in unstrained form is at most 115% of the internal diameter of the reactor tube, and of a foam plug in unstrained form is at most 200% of the internal diameter of the reactor tube.

Before starting the loading of the new catalyst into the reactor tubes, we usually add an inspection step to assure that all the tubes are actually and successfully empty, reducing the risk that a tube has been overlooked by any of the treatment steps described, or that a plug or other solid material has remained inside a tube. The inspection may be a visual inspection, typically using light coming in from one end of the tube, typically from the bottom, and a person inspecting the reactor tube from the other end, typically from the top. A suitable inspection method is described in WO 2006/131557, whereby one or more light sources are introduced into the reactor bottom. In addition or as an alternative thereto, and preferably before the visual inspection, a device comprising a laser light source may be applied to one end of the tube, most conveniently to the top of the tube, and its laser light beam may be directed inside the tube to verify for any obstruction. In case of an obstruction inside the tube, such as a plug being stuck, the laser device may then not only detect the obstruction, but may also measure the distance between the plug and the end of the tube, thereby indicating at what distance inside the tube further mechanical cleaning should be applied.

Other indirect methods for checking the emptiness of the reactor tubes are pressure drop measurements, pushing a rod through each tube and/or checking for air flow by pulling vacuum or putting air pressure on the tubes.

In case of plugging of the tube the obstruction may be removed by applying air pressure followed by pushing the plug with a rod out of the tube. We then typically apply such further mechanical cleaning in that tube, starting from the location indicated by the laser device or determined by an alternative method, and continuing to the other end of the reactor tube. We usually verify the effectiveness of the additional mechanical cleaning by again pushing a plug through the tube, as explained before. Optionally the inspection, mechanical cleaning and plug pushing steps are repeated until no more plugs are stuck in any of the reactor tubes. In order to mark the tubes that have been inspected, and distinguish the tubes that require additional interventions and/or which have already had additional treatment, we usually visually label the tubes after the inspection and/or the intervention. In order to also avoid ingress of undesired material into a tube we conveniently apply visually labelled tube closures into the end of the tube. Suitable closures are described in U.S. Pat. No. 4,701,101 and WO 2006/131556.

When a reactor tube is found clean and suitable to receive the more active catalyst, typically when all tubes in the reactor have been found clean, the more active catalyst may be loaded into the reactor tubes. Typically first a catalyst bed support is introduced into the bottom of the tube. The support is usually porous, and we prefer to use a metal spring in the shape of a conical helix, as described above, because these are easy to insert in a minimum of time, provide ample passage for the process stream during operation, and are readily pushed out again during the vacuuming step of the present invention.

For the loading of the catalyst, we usually employ a loading machine or filling machine, such as described in U.S. Pat. No. 4,402,643, WO 98/14392, DE 19934324, WO 2005/089924 or US 2007/224095. We prefer to use a loading machine comprising a substantially closed filling chamber. In one embodiment of the present invention, the process further comprises removing air borne catalyst dust from the substantially closed filling chamber by the removal of air from the filling chamber and more preferably further comprises filtering the air removed from the filling chamber to collect air borne catalyst dust before further disposal of the air. This brings the advantage that the level of catalyst dust is reduced in the working area of the personnel performing the filling operation.

The bed of the more active catalyst, once it is loaded into the reactor tubes, is preferably layered, usually starting with a highly selective but lower activity catalyst at the top of the tube, and with catalysts having increasing activity in the layers located further down the tube. In one embodiment of the present invention, the more active catalyst bed comprises from 2 to 6 layers of catalyst, more typically 3 and preferably 4 or even 5 layers, whereby the selectivity or the activity of at least two catalyst layers is different. It has been found that the process becomes more stable as the number of layers is increased, and this allows the process to operate stably at higher loadings of the organics in the reaction mixture, i.e. further into the explosive regime, and hence gain capacity. Also the overall selectivity to the desired product may be increased.

The advantages of the layered catalyst bed may be more fully exploited when the structure of the catalyst bed in each of the tubes is more uniform, because then the reactor may be operated closer to its economic optimum and its operational limits. In order to improve uniformity of the catalyst loading, the process of the present invention therefore further comprises verifying the loaded height of at least one layer of the more active catalyst in a reactor tube. We usually verify the height of all the layers of catalyst individually after their loading, and more preferably in all the reactor tubes. Verifying the height of a layer of catalyst after loading may be performed using the laser device described above. We conveniently verify the loading height of a catalyst layer in a tube by lowering a marked stick or tube into the reactor tube until it reaches the top of the catalyst layer.

When the height of the catalyst layer in a reactor tube is outside a range of +/−5% of the targeted height for the bottom layer, +/−3.5% of the targeted combined height for the bottom two layers and +/−2.5% of the targeted combined height for three and/or more layers from the bottom, we usually correct the loading of that reactor tube. For that purpose, we typically mark the tube for correction after having determined the excessive deviation in loaded catalyst height relative to the targeted height. Subsequent correction of the loaded catalyst height may be done for instance by removing the catalyst completely from the tube, followed by renewed loading of the layer or successive layers into that tube. A simpler alternative is by removing or adding small quantities of catalyst, which we conveniently apply in case of a deviation that is at most 2% from the targeted height, preferably at most 1% and more preferably at most 0.5% from the targeted height.

Another method for verifying whether the catalyst loading achieves an appropriate uniformity of the bed over the large number of reactor tubes, is by measuring the pressure drop over the reactor tubes, preferably over each reactor tube, after loading at least one layer of the new catalyst charge and more importantly after completion of all the catalyst loading, alternatively of the entire solids loading in the reactor tube. The advantage of this method is that it may detect tubes containing void spaces or preferential flow channels inside any of the loaded layers, which may lead to a flow maldistribution over the reactor, and which may not be detected by the height verification method described before. In order to further improve uniformity of the catalyst loading, we prefer to perform this pressure drop verification in addition to the height verification method. The pressure drop over the catalyst is conveniently measured by applying a well determined air flow through the reactor tube, preferably with a rate of 1.5

Nm3/hr/tube, more preferably 2 Nm3/hr/tube, even more preferably 3 Nm3/hr/tube and most preferably 4 Nm3/hr/tube, and measuring the pressure drop that is needed in order to push that flow of air through the reactor tube. We usually first measure the pressure drop for a limited number of tubes, such as 300, to determine a target average pressure drop and based thereon set the lower and upper limits for the acceptable pressure drop range. This range is usually ±2.5% of the average, preferably ±2.0%, even more preferably ±1.8% and most preferably ±1.5% of the average. When the pressure drop of a tube is found to be outside the preset range for the given air flow, we typically do a correction of the loading in that tube, which is done by either removing the catalyst completely followed by renewed loading of the successive layers, or by removing or adding small quantities of catalyst, the latter usually applied only in case a deviation is determined that is at most 2% from the target pressure drop, preferably at most 1% and more preferably at most 0.5% from the target pressure drop.

In an embodiment of the present invention therefore, the process further comprises verifying the pressure drop of at least one layer of the more active catalyst in a reactor tube, preferably with further details on the pressure drop verification as explained. We prefer to add a layer of inert catalyst support material, such as ceramic balls or rings, the latter being preferred because of their lower pressure drop, on the top of the catalyst. This is preferably done after the corrections have been made for height and pressure drop of the actual catalyst loading. The layer of inert material in the top of the reactor tube, which typically is the inlet side for the gas mixture containing the reactants, brings the advantage that any entrained liquid o-xylene droplets in the gas mixture have an opportunity to vaporize on the hot inert material before they can reach the active catalyst. In addition, the layer of inert material provides a further preheat zone for the o-xylene/air mixture.

When the new catalyst bed has been loaded as desired, the tubular reactor may subsequently be commissioned. The process of the present invention therefore may further comprise taking the tubular reactor containing the more active catalyst into production service, and producing phthalic anhydride.

In the production of phthalic anhydride, the reaction product exiting the tubular reactor containing the bed of oxidation catalyst is a hot gas mixture containing amongst others nitrogen, $CO_2$, and the desired phthalic anhydride. The reaction product is typically first cooled in a gas cooler, whereby most conveniently steam may be generated on the coolant side. The phthalic anhydride is usually recovered from the cooled reaction product by (de)sublimation in a switch condenser, a phase change that also may be called condensation, whereby the phthalic anhydride is collected as a solid on the switch condenser surface, usually the heat exchanger tubes, which are typically finned on the gas side to improve the heat transfer. The switch condenser is cooled with a cooling fluid, typically a thermal fluid or hot oil, capable of withstanding the high temperatures that are employed. After having been in collecting service, building up a layer of solid phthalic anhydride, typically on the outer surface of the finned exchanger tubes, the switch condenser may be switched from collecting service to melting service. Hereby the gas flow through the switch condenser is usually discontinued and typically the cooling fluid is replaced by a heating fluid, usually the same thermal fluid or hot oil but now after heating, such that the phthalic anhydride melts and forms a liquid, and the liquid phthalic anhydride is drained and collected for further processing.

We conveniently use an additional condensing step, upstream of the switch condensers. In an embodiment of the present invention, the process further comprises recovering phthalic anhydride from the reaction product mixture by a precondenser condensing phthalic anhydride as a liquid followed by a switch condenser collecting phthalic anhydride as a solid. The addition of a precondenser provides the advantage that the gaseous mixture is brought outside the explosive limits by reducing the concentration of the explosive components and by lowering the operating temperature to below the minimum ignition temperature for the resulting gaseous mixture, and this before the gas mixture enters the switch condensers. The precondenser usually also contains finned tubes, and may be cooled with any type of cooling medium, but we prefer to use hot water because it allows to avoid the occurrence of spots having too low temperatures and having the ability to control the precondenser outlet temperature within a narrow range. The outlet of the precondenser is preferably kept at a temperature of at least 137° C.

We have however found that the pressure drop over such precondenser may increase during operation. This increases the operating pressure in the reactor and in the feed preparation zone, where the ortho-xylene or naphthalene typically is vaporised as a hot liquid into a preheated and pressurised stream of oxygen-containing gas, usually air. As said before, this increased operating pressure reduces the stability of the process and the reactor catalyst, and may require that the process is operated at a lower organic loading in the reactor feed, and hence at a lower capacity. We have now found that this pressure drop may be caused by plugging and fouling, probably of heavy byproducts from the reaction, such as trimellitic anhydride or pyromellitic anhydride, formed by the oxidation of their respective precursors which may be present in small quantities in the organic feed of the process, and which have a much higher melting point than phthalic anhydride. We have also found that an increased pressure drop over the precondenser may be reduced again, and this during continuous operation without having to decommission the precondenser. We have found that with a particular precondenser outlet temperature operating strategy, the negative effects of a higher precondenser pressure drop may be alleviated and the pressure drop may be stabilised at a low and acceptable level. The invention therefore further provides for a process for the production of phthalic anhydride, such as the process of the present invention as disclosed above, wherein the temperature at the outlet of the precondenser is first raised and subsequently returned to its original level. We believe that during operation with a constant precondenser outlet temperature heavy byproducts may accumulate as solids in the precondenser and build up pressure drop by fouling. The fouling may melt during a shutdown of the precondenser, and may therefore not be noticed by an inspection after shutdown, because the particular process section may have been exposed to a higher temperature, such as 160° C., before the ultimate shutdown. We have observed that the pressure drop over the precondenser may be reduced again by first raising the precondenser outlet temperature, and subsequently returning it to its original value. We believe that the temperature swing causes a variation of the amount of liquid phthalic anhydride that is condensed on the process side in the precondenser, and, in particular in the second step when the outlet temperature is reduced again and the amount of phthalic anhydride liquid is increased, that the fouling is washed off from the precondenser tubes, in particular off the fins on the tubes, and that thereby the precondenser process side undergoes a type of cleaning treatment. In order to stabilise the precondenser pressure drop at a low and acceptable level over a longer period of time, we prefer that the precondenser outlet temperature is oscillating, more preferably between a maximum and a minimum temperature with a frequency of at least one full cycle per week of operation, even more preferably at least one full cycle per two days, and most preferably at least one full cycle per day of operation. We prefer that the maximum and the minimum temperature are apart with at least 2 degrees C., more preferably at least 4 degrees C., even more preferably at least 5, yet more preferably at least 6 and most preferably at least 7 degrees C. We prefer that the maximum precondenser outlet temperature is at most 150° C., more preferably at most 149° C., even more preferably at most 147° C., and most preferably at most 144° C., and also preferably the minimum temperature being at least 135° C., more preferably at least 137° C. Our most preferred operating strategy for the precondenser is to have its outlet temperature swing once daily back and forth between 144° C. and 137° C.

The phthalic anhydride produced according to the invention may be used for esterification with an alcohol or an alcohol mixture to produce the corresponding di-ester. Suitable esterification processes are disclosed in WO 2005/021482, WO 2006/012989, WO 2008/110305 and WO 2008/110306. The alcohol may be a secondary alcohol, such as isopropanol, but is preferably a primary alcohol. Suitable primary alcohols are $C_1$-$C_{13}$ primary alcohols, and may be branched or unbranched, such as methanol, ethanol, n-propanol, n-butanol, isobutanol, isohexanol, isoheptanol, iso-octanol, 2-ethyl-hexanol, isononyl alcohol, 2,4-dimethyl heptanol, normal decanol, isodecanol, isoundecyl alcohol, 2-propyl heptanol, undecyl-dodecyl alcohol, isotridecyl alcohol and mixtures thereof. Dimethylphthalate and diethylphthalate are preferred products for personal care applications. The phthalates with alkyl chains having 4 or more carbon atoms, up to 13, are used as plasticizers for polyvinyl chloride (PVC).

The process of the present invention therefore may further comprise esterifying the phthalic anhydride with an alcohol or an alcohol mixture to produce a phthalate ester. The process of the invention is suitable for producing all these phthalates, in particular those produced from alcohols or alcohol mixtures having an average of 4 to 13 carbon atoms, especially alcohols or alcohol mixtures containing molecules having a branched alkyl chain, preferably alcohols having 8 to 10 carbon atoms, especially those having an average of approximately 9 carbon atoms, such as those designated as DOP, DINP, DIDP and DTDP. Di-isononyl phthalate (DINP) is highly preferred as a PVC plasticiser, and so is di-isodecyl phthalate (DIDP). Also suitable is di-propylheptyl phthalate (DPHP) These higher molecular weight phthalates provide a higher permanence in the flexible PVC end product compared to the lower molecular weight equivalents such as di-2-ethylhexyl phthalate (DEHP or also called DOP). Di-isotridecyl phthalate (DTDP) is preferred in low volatility applications such as special purpose Wire and Cable manufacture. These phthalate esters may further be hydrogenated to form their corresponding 1,2-cyclohexane dicarboxylic acid esters, such as e.g. di-isononyl cyclohexanoate, as disclosed in WO 2003/029339 The latter hydrogenation step may be performed by techniques known in the art, such as by using the processes described in EP 1042273 or WO 2004/046078. The process of the invention may therefore further comprise hydrogenating the phthalate ester to produce a 1,2-cyclohexane-dicarboxylic acid ester, in particular having isononyl alkyl chains.

The primary alcohols used in the esterification may be so-called oxo-alcohols, produced by the hydroformylation of olefins, when necessary followed by hydrogenation of the aldehyde intermediate. Suitable processes for hydroformylation to produce alcohols are disclosed in WO2005/058787, WO 2008/128852, WO 2008/122526, or in copending patent applications PCT/EP2009/005995 and PCT/EP2009/005996, and suitable processes for aldehyde hydrogenation are disclosed in WO2005/058782.

The invention is now further illustrated with the following examples. These examples describe how used catalyst is removed from the reactor tubes of a tubular reactor in a process for the production of phthalic anhydride wherein a gaseous mixture of ortho-xylene and air is contacted with an oxidation catalyst comprised in vertical tubes of a tubular reactor.

The examples describe different methods that were practiced for the removal of the used catalyst from the reactor tubes by vacuum hosing from the top of the reactor tube. The reactor tubes in the examples have an internal diameter of 25 mm and are 3.4 m long. The catalyst particles in the examples had the shape of hollow cylinders having the dimensions of 7×7×4 mm (OD×H×ID).

Example 1 (Comparative)

The catalyst removal was performed by workers each using one rigid PVC plastic suction pipe. The PVC suction pipes were at least 3.5 m long, having an outer diameter of 19 mm and an inner diameter of 17 mm and were connected with a flexible hose to a suction manifold providing the vacuum. During the vacuum hosing, the workers did experience build-up of static electricity. The static electricity nuisance was particularly strong when electrical conduit PVC pipe was used and was less strong when grey water or sewer PVC pipe was used. Due to the length of the suction pipe and the rigidity of the PVC, a free height of at least 4 m above the tube sheet was required to allow for handling the pipes. In order to create this free height, the top head had to be dismantled from the tubular reactor for the catalyst removal.

We found that clusters of bridged catalyst particles became stuck in the opening of the PVC suction pipe. Upon exertion of extra mechanical force to remove the blockage, damage was frequently caused to the tip of the PVC suction pipe. By cutting off the tip of the suction pipe at an angle of 45 degrees relative to the length axis of the PVC suction pipe, the frequency of blockage was reduced and it was a lot easier to remove the blockage without damaging the pipe. Clusters of sintered catalyst particles remained very difficult to remove with the PVC suction pipes, because the PVC pipe frequently fractured at the tip upon trying to break the sintered material. The spring coils supporting the catalyst bed at the bottom of the reactor tubes were removed by interrupting the suction air flow through the suction pipe and pushing the coils out with the pipe. Also this action frequently caused damage to the tip of the PVC suction pipe.

Example 2 (Comparative)

The catalyst removal was performed by workers each using one stainless steel suction pipe. The suction pipes were at least 3.5 m long, having an outer diameter of 22 mm and an inner diameter of 19 mm and were connected with a flexible hose to the suction manifold providing the vacuum. The catalyst removal operation went very slow due to the lack of open area between the suction pipe outer wall and the reactor tube inner wall. The air flowing down through the annular space between suction pipe and reactor tube was causing excessive pressure drop, resulting in a lower air pressure at the tip of the suction pipe, and insufficient velocity of the air up through the suction pipe to readily move the catalyst into the suction tube. The use of stainless steel caused frequent fracture of the ceramic catalyst support rings, which impaired the recycling of these rings for the manufacture of new catalyst.

It also caused contamination of the active mass that was recovered from the ceramic rings. The workers did not experience any build-up of static electricity during the use of the stainless steel suction pipes. No damage was experienced at the tip of the stainless steel suction pipe throughout the catalyst removal operation. Due to the length of the suction pipe and the lack of flexibility of the stainless steel pipe, a free height of at least 4 m above the tube sheet was required to allow for handling the pipes. This also required dismantling of the reactor top head.

Example 3 (Comparative)

The catalyst removal was performed by workers each using one stainless steel suction pipe. The pipes were at least 3.5 m long, having an outer diameter of 20 mm and an inner diameter of 18 mm and were connected with a flexible hose to the suction manifold providing the vacuum. The tip of the suction pipe was cut off at an angle of 45 degrees relative to the length or longitudinal axis of the suction pipe. Both the normal and sintered catalyst was readily removed with only occasional blockage due to a cluster of bridged catalyst particles becoming stuck at the tip of the suction pipe. The cluster was easily broken up and removed without damaging the pipe. The use of stainless steel caused frequent fracture of the ceramic catalyst support rings, which impaired the recycling of these rings for the manufacture of new catalyst. It also caused contamination of the active mass that was recovered from the ceramic rings. The workers did not experience any build-up of static electricity during the use of the stainless steel suction pipes. Due to the length of the suction pipe and the lack of flexibility of the stainless steel pipe, a free height of at least 4 m above the tube sheet was required to allow for handling the pipes. This also required dismantling of the reactor top head.

Example 4 (According to the Invention)

The catalyst removal was performed by a worker who was using simultaneously two flexible plastic suction pipes, one in each hand. The pipes were made from Polyamide-Nylon 11/12 according to DIN 73378, with an outer diameter of 22 mm and an inner diameter of 18 mm. The pipe material had a U-notched Charpy impact strength according to ISO 179 of more than 5 kJ/m$^2$, a Shore D hardness according to ISO 868 of about 47, a flexural or elastic modulus according to DIN EN ISO 527 of about 1.15 GPa and an electric resistivity at room temperature of less than $10^{15}$ Ohm.cm. The workers did not experience any build-up of static electricity during the use of suction pipes made from this material. The tips of the tubes were cut off at an angle of 45 degrees relative to the length axis of the tube. Fracturing of the ceramic catalyst support rings was minimal The spring coils acting as bed support were easily removed by pushing them out with the suction tubes, without interrupting the suction flow. No significant damage was observed, to the tip of the suction pipes, from vacuuming the catalyst particles nor from pushing the spring coils out the bottom of the tube. The minimum required free height above the flexible tube sheet was reduced to 0.3-1 m, which did not anymore require dismantling of the reactor top head, which represented a significant savings of intervention time and costs. The catalyst removal in this example became sufficiently smooth and flawless such that the same operator could now control two suction pipes simultaneously, one in each hand. The simultaneous use of two flexible suction pipes by the same operator resulted in a reduction of the total work time required for the catalyst removal by 30% for the same reactor.

The above examples demonstrate the benefit of using, for the vacuum hosing of used catalyst from a tubular reactor comprised in a process for the production of phthalic anhydride, a suction pipe comprising, at least at its tip and possibly all through the suction pipe, a material having a particular balance of properties, more specifically higher notched Izod impact strength or a U-notched Charpy impact strength or resistance than those properties of unmodified rigid PVC, and at the same time a Shore D hardness that is lower than this of stainless steel. Further advantages are obtained when a material is selected having an electric resistivity at room temperature of at most $10^{15}$ Ohm.cm and/or an elastic modulus below 2.7 GPa. Further advantages have been demonstrated for selecting a suction pipe having particular outer diameter dimensions.

Example 5

The tubes of the reactor from which the used catalyst was removed as in Example 4 was, after all reactor tubes had been emptied, further cleaned by running through the tubes and from the top of the reactor a rotating single knitting stainless steel brush, driven by an air motor, while a vacuum was applied to the bottom of the reactor. The reactor tubes that were not operated on were capped off by a plastic closure made from polypropylene with the colours white, black, green and red, with a cylindrical outer diameter of 23 mm, inner diameter of 20 mm, 30 mm height and a cap on the cylinder of 32 mm. Subsequently and while the vacuum was maintained on the bottom of the reactor, a cylindrical felt plug was pushed through the tubes, from the top and assisted with air pressure from the top of the reactor. Cleanliness of the reactor tubes was inspected visually from the top, while a light source was introduced in the bottom compartment of the reactor, below the bottom tubesheet. A laser light source was used to detect and to locate obstructions inside the tubes. Each empty and clean tube was provided with a conical helix spring in the bottom, obtained from Augsburger Federnfabrik GmbH in Koenigsbrunn, Germany. Fresh catalyst was then loaded into the reactor, and the loading was performed using a filling machine similar to what is described in US 2007/224095. The bed in each tube consisted, starting from the bottom of the tube, of a height of about 0.7 m of catalyst IV, 0.7 m of catalyst III, 0.6 m of catalyst II, 1.2 m of catalyst I, and after pressure drop measurements the tubes had been topped with inert rings of 0.1 m height, In this series, catalyst I is the most selective, and the catalyst selectivity was gradually decreasing down to catalyst IV, while simultaneously the catalysts were increasing in activity. After loading each layer of catalyst or inert material, the height of the loading in each tube was verified by lowering a marked plastic tube into the tube until it reached the top of the last loaded catalyst layer, and the loading was corrected until deviations in height were below 0.5% from the targeted height. After the loading of each layer of catalyst or inert material, the pressure drop over the tubes was verified by applying an air flow of 4 Nm$^3$/hr through each tube from the top, while having atmospheric pressure in the reactor bottom compartment. The loading was corrected until deviations in pressure drop were below 0.5% from the target average pressure drop.

After correct loading of the catalyst bed was established, the reactor was closed and inerted, and subsequently commissioned as part of a process for producing phthalic anhydride from o-xylene and the loading was successfully increase to 90 grams per Nm³ of air. Downstream of the reactor, the process comprised a precondenser cooled by hot water.

During 3 months of operation of the process, an increase in the pressure drop over the precondenser was observed, and this increase forced a limitation of the o-xylene loading to only 84 grams per Nm³ in order to keep the process operating in a stable manner. After a further 5 months of operation, a change of operations was made by introducing a daily temperature swing of the precondenser outlet temperature between 144° C. and 137° C. The pressure drop over the precondenser decreased and stabilised at a lower level, and the o-xylene loading could again be increased to 90 grams per Nm³ of air without affecting the process stability.

Having now fully described this invention, it will be appreciated by those skilled in the art that the invention can be performed within a wide range of parameters within what is claimed, without departing from the spirit and scope of the invention. As understood by those of skill in the art, the overall invention, as defined by the claims, encompasses other preferred embodiments not specifically enumerated herein.

The invention claimed is:

1. A process for the production of phthalic anhydride comprising contacting a gaseous mixture of ortho-xylene or naphthalene and an oxygen-containing gas with an oxidation catalyst comprised in vertical tubes of a tubular reactor, the process comprising after using the catalyst taking the tubular reactor out of production service, removing the used catalyst and loading more active catalyst into the reactor tubes, whereby used catalyst is removed from the reactor tubes by vacuum hosing through a vacuum hose or tube that is introduced into the reactor tube from the top and characterised in that the tip of the vacuum hose or tube comprises a material that has (i) a notched Izod impact strength, according to ASTM D256, of at least 55 J/m, or a U-notched Charpy impact strength at 23° C., according to ISO 179, of more than 5 kJ/m2, and (ii) a Shore D hardness, according to ISO 868, of at most 90.

2. The process according to claim 1 wherein the body of the vacuum hose or tube comprises a material having an elastic modulus, according to DIN EN ISO 527, of less than 2.7 GPa.

3. The process according to claim 1 wherein the body of the vacuum hose or tube comprises a material having an electric resistivity at room temperature of at most 1015 Ohm.cm.

4. The process according to claim 1 wherein the Shore D hardness of the material comprised in the tip of the vacuum hose or tube, according to ISO 868, least 40.

5. The process according to claim 1 wherein the tip of the vacuum hose or tube is slanted in an angle with the longitudinal axis of the hose or tube and in which the angle is in the range of 20-70°.

6. The process according to claim 1 further comprising, after removing the used catalyst from a reactor tube, cleaning the inside of the reactor tube by mechanical action from one end of the reactor tube to remove any remaining catalyst or other solid material.

7. The process according to claim 6 wherein a vacuum is applied on the reactor tube during the mechanical action.

8. The process according to claim 1 further comprising pushing a flexible or compressible plug through the reactor tube.

9. The process according to claim 1 further comprising a visual inspection of the reactor tube to verify for presence of remaining catalyst or other solid material or a plug.

10. The process according to claim 1 wherein the more active catalyst is loaded into the reactor tubes using a loading machine.

11. The process according to claim 1 further comprising taking the tubular reactor containing the more active catalyst into production service, and producing phthalic anhydride.

12. The process according to claim 11 comprising recovering phthalic anhydride from the reaction product gas mixture by a precondenser condensing phthalic anhydride as a liquid followed by a switch condenser wherein phthalic anhydride is deposited as a solid, and wherein the temperature at the outlet of the precondenser is first raised and subsequently returned to its original level.

13. The process according to claim 11 further comprising esterifying the phthalic anhydride with an alcohol or an alcohol mixture to produce a phthalate ester.

14. The process according to claim 13 further comprising hydrogenating the phthalate ester to produce a 1,2-cyclohexane-dicarboxylic acid ester.

* * * * *